(12) United States Patent
Kizaki et al.

(10) Patent No.: US 7,332,312 B2
(45) Date of Patent: Feb. 19, 2008

(54) CARBONYL REDUCTASE, GENE THEREOF AND USE OF THE SAME

(75) Inventors: Noriyuki Kizaki, Takasago (JP); Miho Horikawa, Takasago (JP); Yoshihiko Yasohara, Takasago (JP)

(73) Assignee: Kaneka Corporation, Osaka-Shi, Osaka (JP)

( * ) Notice: Subject to any disclaimer, the term of this patent is extended or adjusted under 35 U.S.C. 154(b) by 0 days.

(21) Appl. No.: 10/512,908

(22) PCT Filed: Apr. 30, 2003

(86) PCT No.: PCT/JP03/05500

§ 371 (c)(1),
(2), (4) Date: Jul. 11, 2005

(87) PCT Pub. No.: WO03/093477

PCT Pub. Date: Nov. 13, 2003

(65) Prior Publication Data
US 2006/0046289 A1 Mar. 2, 2006

(30) Foreign Application Priority Data
Apr. 30, 2002 (JP) .............................. 2002-128648

(51) Int. Cl.
*C12N 1/20* (2006.01)
*C12N 9/02* (2006.01)
*C12N 1/21* (2006.01)
*C12N 15/00* (2006.01)
*C07H 21/04* (2006.01)
*C12P 7/22* (2006.01)

(52) U.S. Cl. ...................... 435/135; 456/189; 456/69.1; 456/252.3; 456/252.8; 536/23.2; 435/156; 435/320.1; 435/252.33; 435/325

(58) Field of Classification Search ...................... None
See application file for complete search history.

(56) References Cited

U.S. PATENT DOCUMENTS

| 5,266,485 A | 11/1993 | Sawa et al. |
| 6,642,387 B2 | 11/2003 | Amano et al. |

FOREIGN PATENT DOCUMENTS

| EP | 0 493 617 A1 | 7/1992 |
| EP | 0 493 617 B1 | 7/1992 |
| EP | 1 153 919 A1 | 11/2001 |
| JP | 4-218384 A | 8/1992 |
| JP | 8-103269 A | 4/1996 |
| JP | 11-215995 A | 8/1999 |
| WO | WO 00/48997 A1 | 8/2000 |

OTHER PUBLICATIONS

Itoh et al. ( Eur. J. Biochem. 269, 2002, pp. 2394-2402).*
Itoh et al. ( Eur J. Biochem. 2002, Mar. 22, 269, pp. 2394-2402.*
Nakamura, K., et al., "Asymmetric Reduction of Ketones by the Acetone Powder of Geotrichum Candidum," *J. Org. Chem.*, 1998, vol. 63, pp. 8957-8964.
International Search Report From Corresponding International Application No. PCT/JP03/05500, dated Aug. 26, 2003, 2 pages.
Patent Cooperation Treaty International Preliminary Examination Report (PCT Article 36 and Rule 70), From Corresponding International Application No. PCT/JP2003/005500, Dated Feb. 20, 2004, 4 pages.
Wada, M. et al., "Purification and Characterization of NADPH-Dependent Carbonyl Reductase, Involved in Stereoselective Reduction of Ethyl 4-Chloro-3-Oxobutanoate, from *Candida magnoliae*," *Bioscience Biotechnology Biochemistry*, vol. 62, No. 2, Feb. 1998, pp. 280-285.
Kizaki, N. et al., "Synthesis of Optically Pure Ethyl (S)-4-Chloro-3-Hydroxybutanoate by *Escherichia coli* Transformant Cells Coexpressing the Carbonyl Reductase and Glucose Dehydrogenase Genes," *Applied Microbiology and Biotechnology*, vol. 55, No. 5, May 2001, pp. 590-595.
Kizaki, Noriyuki, "Purification and Characterization of a Yeast Carbonyl Reductase for Synthesis of Optically Active (R)-Styrene Oxide Derivatives," *Bioscience Biotechnology and Biochemistry*, vol. 69, No. 1, Jan. 2005, pp. 79-86.
Supplementary European Search Report from Application No. EP 03 72 0993, Mar. 21, 2006, 4 pages.
Visser, H., et al. "Cloning and characterization of an expoxide hydrolase-encoding gene from *Rhodotorul glutinis*," *Applied Microbiology And Biotechnology*, 53(4):415-419 (2000).

* cited by examiner

*Primary Examiner*—Rebecca E. Prouty
*Assistant Examiner*—M. Y. Meah
(74) *Attorney, Agent, or Firm*—Brinks Hofer Gilson & Lione

(57) ABSTRACT

The present invention provides a novel polypeptide forming (R)-2-chloro-1-(3'-chlorophenyl)ethanol, a polynucleotide coding for said polypeptide, and use of the same.

The present invention relates to a polypeptide having the following physical and chemical properties (1) to (4):

(1) activity: acting on 2-chloro-1-(3'-chlorophenyl)ethanone with NADPH or NADH as a coenzyme, to form (R)-2-chloro-1-(31-chlorophenyl)ethanol;
(2) optimum pH for activity: 5.0 to 6.0;
(3) optimum temperature for activity: 40° C. to 50° C.;
(4) molecular weight: about 40,000 as determined by gel filtration analysis, about 30,000 as determined by SDS polyacrylamide gel electrophoresis analysis. The present invention also relates to a polypeptide comprising the amino acid sequence shown under SEQ ID NO:1 in the sequence listing, a polynucleotide coding for said polypeptide, and a transformant producing said polypeptide at high levels.

18 Claims, 2 Drawing Sheets

Fig. 1

```
         10        20        30        40        50        60        70        80
ATGCCCGCAGCAAAGACTTACTTCATCTCGGGTGCGTCCAGCGAAAACCAGGTCTATCCGGTCCAGGTGCACACAGACCC
 M  P  A  A  K  T  Y  F  I  S  G 90       100       110       120       130       140       150       160
GCTGACACAGCTTCACTCGCGCAGGCGCCTCGCGCGGCCTCGGATTGGGCTACACCCGTGAACTGCTCGCCTCGAACCCT
             A  S  R  G  L  G  L  G  Y  T  R  E  L  L  A  S  N  P 170       180       190       200       210       220       230       240
GACGTCCGAGTCGTGGCCGGAGTTCGCAACCCTTCTAACGCCCAGCTCTTGGACGCCCTCGCCGCCGAACCCGCCAACAA
 D  V  R  V  V  A  G  V  R  N  P  S  N  A  Q  L  L  D  A  L  A  A  E  P  A  N  K 250       260       270       280       290       300       310       320
AGGCCGAGTTCACGTCATCGCGTGGGACGTCGACCACGAGGACAAGGTCCGCGAGTCGGCGCGCGAGTTGGAAACAAACC
 G  R  V  H  V  I  A  W  D  V  D  H  E  D  K  V  R  E  S  A  R  E  L  E  T  N  P 330       340       350       360       370       380       390       400
CGTTCGTGAAAGAGTCTGGAATCGACACCGTCATCGTCAACGCAGGCGTCTTTGTCGGCGGACACAAGCCGCCCGCCGAG
 F  V  K  E  S  G  I  D  T  V  I  V  N  A  G  V  F  V  G  G  H  K  P  P  A  E 410       420       430       440       450       460       470       480
ATGTGAGTCCGTAGAACCCGCGGCCGGTGACGAACGCCCCGATCAATAAGTCTCAACAGAGCCACCGGAGCTGAGCGAGA
 M 490       500       510       520       530       540       550       560
AACGTACCCACAGGTCGATGGACGACCTGCGCGCCAACTTCCGGACCAACGTCGAGGGAGCCATCTTTACCGTCCAGTAC
               S  M  D  D  L  R  A  N  F  R  T  N  V  E  G  A  I  F  T  V  Q  Y 570       580       590       600       610       620       630       640
CTCCACCCGCTGCTTGAGCGTGGGCAGGCGAAGCAGATCTTCTTCATCAGCTCGATCGTCGGGTCGATGCAGGGCTTTTA
 L  H  P  L  L  E  R  G  Q  A  K  Q  I  F  F  I  S  S  I  V  G  S  M  Q  G  F  Y 650       660       670       680       690       700       710       720
CTCGCAGCTGTCGGCCGGCGTCTCTTGTGAGCACGCTTCCCCCCTGCCGCCTTTGGTACACGAGCTCGACTGACGCCCAC
 S  Q  L  S  A  G  V  S 730       740       750       760       770       780       790       800
ATTCCCCCACGAACAGACTCCATGTCCAAGGTTAGTCCCGCTCGAGCTCTTGCGGGCCACCGGGAACCTGACCGGCTGCG
               S  M  S  K 810       820       830       840       850       860       870       880
CCGAAAACTGCGTCACAGGCCGCCCTGAACATGTACGGCGTCAAGCTCGCGCGCGAGCTCGGCGACAAGGGCTACACGGT
 A  A  L  N  M  Y  G  V  K  L  A  R  E  L  G  D  K  G  Y  T  V 890       900       910       920       930       940       950       960
CCTCCTGATCCACCCGGGCTACGTCAAGACCGACATGGTGCGCCTTCGTTCGCTTCAAAGCGAGTAATCGCGAATCCTTC
 L  L  I  H  P  G  Y  V  K  T  D  M 970       980       990      1000      1010      1020      1030      1040
CCCCTCGCTGACATGGTTTCCCTCCGGCAGAACAACTTTGACGGAGGCGGAGACATCACCACGGAGGAAGCGGTTAGCCT
                               N  N  F  D  G  G  D  I  T  T  E  E  A  V  S  L 1050      1060      1070      1080      1090      1100      1110      1120
CGCGTGCGTGACAACGTATCTCCGTGATCAGGAGCACGGGACCTCGCAAGCTGATCATCCGCGCTCGCGACAGGACGAAA
 A                                                                       T  K 1130      1140      1150      1160      1170      1180      1190      1200
AACGTCTTCCTCGCCGCCACTCCCGAGTGGAACGGCCGCTACATCGACTACGAGGGCAAGACCGTGCCGTGGTAG
 N  V  F  L  A  A  T  P  E  W  N  G  R  Y  I  D  Y  E  G  K  T  V  P  W  *
```

CARBONYL REDUCTASE, GENE THEREOF AND USE OF THE SAME

RELATED APPLICATIONS

This application is a nationalization of PCT Application No. PCT/JP03/05500 filed Apr. 30, 2003. This application claims priority from Japanese Patent Application No. 2002-128648 filed on Apr. 30, 2002.

TECHNICAL FIELD

The present invention relates to a polypeptide having activity in asymmetrically reducing 2-chloro-1-(3'-chlorophenyl)ethanone represented by the formula (1):

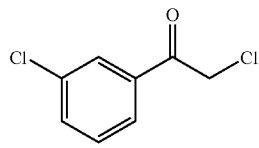

(1)

to form (R)-2-chloro-1-(3'-chlorophenyl)ethanol represented by the formula (2):

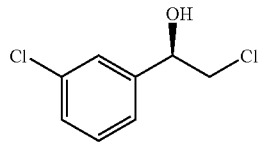

(2)

as isolated from a microorganism having such activity, a polynucleotide coding for said polypeptide, an expression vector containing said polynucleotide, and a transformant transformed with said expression vector.

The present invention also relates to a method for producing optically active alcohols, in particular optically active 1-phenylethanol derivatives or optically active 3-hydroxy ester derivatives using said transformant. Such optically active 1-phenylethanol derivatives or optically active 3-hydroxy ester derivatives are compounds useful as synthetic materials for such as medicines and agricultural chemicals.

BACKGROUND ART

As for the methods for producing optically active 1-phenylethanol derivatives, there have been disclosed:

1) the method which comprises allowing a microorganism belonging to the genus *Ashbya* or *Ogataea* or processed products thereof, for instance, to act on a 2-halo-1-(substituted phenyl)ethanone to form an optically active 2-halo-1-(substituted phenyl)ethanol (Japanese Kokai Publication Hei-04-218384 and Japanese Kokai Publication Hei-11-215995), and 2) the method which comprises allowing dry cells of *Geotrichum candidum* to act on a 1-(substituted phenyl)ethanone to form an optically active 1-(substituted phenyl)ethanol (J. Org. Chem., 63, 8957 (1998)).

As for the method for producing optically active 3-hydroxy ester derivatives, there has been disclosed:

3) the method which comprises allowing a recombinant *Escherichia coli* as obtained by introduction of a *Sporobolomyces salmonicolor*-derived aldehyde reductase gene to act on a 4-substituted acetoacetic acid ester to form an (R)-4-substituted-3-hydroxybutyric acid ester (Japanese Kokai Publication Hei-08-103269).

However, all of these methods allow only a low substrate charge concentration or give a low rate of conversion from substrate to product. Thus, more efficient production method has been desired.

SUMMARY OF THE INVENTION

In view of the above-mentioned state of the art, the present invention has for its object to provide a polypeptide useful in the production of optically active 1-phenylethanol derivatives or optically active 3-hydroxy ester derivatives, a polynucleotide coding for said polypeptide, an expression vector containing said polynucleotide, and a transformant transformed with said expression vector.

The present invention also has for its object to provide a method for efficiently producing optically active 1-phenylethanol derivatives or optically active 3-hydroxy ester derivatives using said transformant.

The present inventors isolated a polypeptide having activity in asymmetrically reducing 2-chloro-1-(3'-chlorophenyl)ethanone to form (R)-2-chloro-1-(3'-chlorophenyl)ethanol, from a microorganism having such activity, and found that use of said polypeptide make it possible to efficiently produce not only (R)-2-chloro-1-(3'-chlorophenyl)ethanol but also useful optically active alcohol, for example optically active 1-phenylethanol derivatives, such as (S)-1-(2'-fluorophenyl)ethanol, and optically active 3-hydroxy ester derivatives, typically ethyl (R)-4-chloro-3-hydroy butyrate. They also succeeded in isolating a polynucleotide coding for said polypeptide and further in creating an expression vector and a transformant. Thus, the present invention has been completed.

That is, the invention provides a polypeptide capable of asymmetrically reducing 2-chloro-1-(3'-chlorophenyl)ethanone to form (R)-2-chloro-1-(3'-chlorophenyl)ethanol.

The invention also provides a polynucleotide coding for the above polypeptide.

The invention further provides an expression vector containing the above polynucleotide.

The invention further provides a transformant capable of producing the above polypeptide at high levels.

The invention still further provides a practical method for producing optically active 1-phenylethanol derivatives or optically active 3-hydroxy ester derivatives, typically (R)-2-chloro-1-(3'-chlorophenyl)ethanol, (S)-1-(2'-fluorophenyl)ethanol and ethyl (R)-4-chloro-3-hydroxybutyrate, using said transformant.

DETAILED DESCRIPTION OF THE INVENTION

In the following, the invention is described in detail.

Usable as the polypeptide of the invention is any of those polypeptides having activity in asymmetrically reducing 2-chloro-1-(3'-chlorophenyl)ethanbne represented by the formula (1):

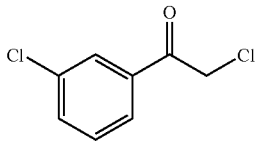

to form (R)-2-chloro-1-(3'-chlorophenyl)ethanol represented by the formula (2):

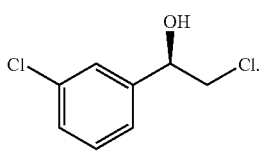

Such a polypeptide can be isolated from a microorganism having the activity mentioned above. The microorganism to be used as the source of the polypeptide is not particularly restricted but there may be mentioned, for example, yeasts of the genus *Rhodotorula*, and *Rhodotorula glutinis* var. *dairenensis* IFO 0415 is particularly preferred.

The microorganism producing the polypeptide of the invention may be a wild strain or variant. A microorganism derived by a genetic engineering technique, such as cell fusion or gene manipulation can be used as well. A genetically engineered microorganism producing the polypeptide of the invention can be obtained, for example, by a method comprising the step of isolating and/or purifying such polypeptide and determining a part or the whole of the amino acid sequence thereof, the step of determining the polynucleotide base sequence coding for the polypeptide based on that amino acid sequence, and the step of obtaining a recombinant microorganism by introducing that polynucleotide into another microorganism.

The polypeptide of the invention can be purified from the microorganism containing that polypeptide in the conventional manner. For example, cells of the microorganism are cultivated in an appropriate medium, and cells are then collected from the culture by centrifugation. The cells obtained are disrupted using a sonicator, for instance, and the cell residue is removed by centrifugation, whereby a cell-free extract is obtained. The polypeptide can be purified from this cell-free extract by using such techniques, either singly or in combination, as salting out (e.g. by ammonium sulfate precipitation, sodium phosphate precipitation, etc.), precipitation using a solvent (protein fractionation precipitation with acetone, ethanol, etc.), dialysis, gel filtration, ion exchange, reversed phase or like column chromatography, and ultrafiltration.

The enzyme activity determination can be carried out by adding the substrate 2-chloro-1-(3'-chlorophenyl)ethanone (1 mM) and the coenzyme NADPH (0.25 mM) and the enzyme to 100 mM phosphate buffer (pH 6.5) containing 0.3% (v/v) of dimethyl sulfoxide and measuring the decrement in absorbance at a wavelength of 340 nm at 30° C.

As the polypeptide of the invention, there may be mentioned, for example, polypeptides having the following physical and chemical properties (1) to (4):

(1) activity: acting on 2-chloro-1-(3'-chlorophenyl)ethanone with NADPH or NADH as a coenzyme, to form (R)-2-chloro-1-(3'-chlorophenyl)ethanol;
(2) optimum pH for activity: 5.0 to 6.0;
(3) optimum temperature for activity: 40° C. to 50° C.;
(4) molecular weight: about 40,000 as determined by gel filtration analysis, about 30,000 as determined by SDS polyacrylamide gel electrophoresis analysis.

As the polypeptide of the invention, there may further be mentioned, for example, (a) a polypeptide comprising the amino acid sequence shown under SEQ ID NO:1 in the sequence listing or (b) a polypeptide comprising the amino acid sequence shown under SEQ ID NO:1 in the sequence listing or an amino acid sequence resulting from substitution, insertion, deletion or addition of at least one amino acid residue in the amino acid sequence shown under SEQ ID NO:1 in the sequence listing and having activity in asymmetrically reducing 2-chloro-1-(3'-chlorophenyl)ethanone to form (R)-2-chloro-1-(3'-chlorophenyl)ethanol.

Polypeptides comprising an amino acid sequence derived from the amino acid sequence shown under SEQ ID NO:1 in the sequence listing resulting from substitution, insertion, deletion or addition of at least one amino acid can be prepared by the conventional method described in Current Protocols in Molecular Biology (John Wiley and Sons, Inc., 1989), and the like. So long as they have activity in asymmetrically reducing 2-chloro-1-(3'-chlorophenyl)ethanone to form (R)-2-chloro-1-(3'-chlorophenyl)ethanol, such polypeptides are included within the definition of the polypeptide of the invention.

While any polynucleotide coding for the above polypeptide can be used as the polynucleotide of the invention, there may be mentioned, for example, (c) the polynucleotide comprising the base sequence shown under SEQ ID NO:2 in the sequence listing or (d) a polynucleotide capable of hybridizing with a polynucleotide comprising the base sequence complementary to the base sequence shown under SEQ ID NO:2 in the sequence listing under stringent conditions and coding for a polypeptide having activity in asymmetrically reducing 2-chloro-1-(3'-chlorophenyl)ethanone to form (R)-2-chloro-1-(3'-chlorophenyl)ethanol.

The polynucleotide capable of hybridizing with a polynucleotide comprising the base sequence complementary to the base sequence shown under SEQ ID NO:2 in the sequence listing under stringent conditions means a polynucleotide obtained by colony hybridization, plaque hybridization, or southern hybridization, for instance, using a polynucleotide comprising the base sequence complementary to the base sequence shown under SEQ ID NO:2 in the sequence listing as a probe. More specifically, there may be mentioned a polynucleotide that can be identified after carrying out hybridization using a filter with colony- or plaque-derived polynucleotides immobilized thereon, in the presence of 0.7 to 1.0 M NaCl at 65° C., and washing the filter with 0.1 to 2×SSC solution (the composition of 1×SSC solution comprising 150 mM sodium chloride and 15 mM sodium citrate) at 65° C. The hybridization can be carried out as described in Molecular Cloning, A laboratory manual, second edition (Cold Spring Harbor Laboratory Press, 1989), and the like.

As the polynucleotide capable of hybridizing, there may be mentioned, specifically, polynucleotides having at least 60%, preferably at least 80%, more preferably at least 90%, still more preferably at least 95%, most preferably at least 99%, homology in sequence to the polynucleotide shown under SEQ ID NO:2 in the sequence listing and, so long as the polypeptides encoded have activity in asymmetrically reducing 2-chloro-1-(3'-chlorophenyl)ethanone to form (R)-2-chloro-1-(3'-chlorophenyl)ethanol, they are included within the definition of the polynucleotide of the invention.

The "homology (%) in sequence" so referred to herein is expressed in terms of the value determined by aligning, in an optimum manner, the two polynucleotides to be compared, determining the number of those sites of coincidence in nucleic acid base (e.g. A, T, C, G, U or I) between the both, dividing the number by the total number of the bases compared, and multiplying the result by 100.

The sequence homology can be calculated, for example, by using the following tools for sequence analysis: Unix-based GCG Wisconsin Package (Program Manual for the Wisconsin Package, Version 8, September, 1994, Genetics Computer Group, 575 Science Drive Madison, Wis., USA 53711; Rice, P. (1996), Program Manual for EGCG Package, Peter Rice, The Sanger Centre, Hinxton Hall, Cambridge, CB10 1RQ, England) and the ExPASy World Wide Web Server for Molecular Biology (Geneva University Hospital and University of Geneva, Geneva, Switzerland).

The polynucleotide of the invention can be obtained from a microorganism having activity in asymmetrically reducing 2-chloro-1-(3'-chlorophenyl)ethanone to form (R)-2-chloro-1-(3'-chlorophenyl)ethanol. As such microorganism, there may be mentioned, for example, yeasts of the genus *Rhodotorula*, and *Rhodotorula glutinis* var. *dairenensis* IFO 0415 may be mentioned as a particularly preferred one.

In the following, an example is described of the method for obtaining the polynucleotide of the invention from a microorganism having activity in asymmetrically reducing 2-chloro-1-(3'-chlorophenyl)ethanone to form (R)-2-chloro-1-(3'-chlorophenyl)ethanol. This example is not restrictive of the scope of the invention, however.

First, partial amino acid sequences of the above-mentioned polypeptide after purification and peptide fragments obtained by digestion of said polypeptide with appropriate endopeptidases are determined by the Edman method. Based on this amino acid sequence information, nucleotide primers are synthesized. Then, the chromosomal DNA of the microorganism to serve as the source of the polynucleotide of the invention is prepared from that microorganism by the conventional method of DNA isolation such as the method described in Current Protocols in Molecular Biology (John Wiley and Sons, Inc., 1989).

Using this chromosomal DNA as a template, PCR (polymerase chain reaction) is carried out using the nucleotide primers mentioned above to thereby amplify part of the polynucleotide coding for the polypeptide. The base sequence of the thus-amplified polynucleotide can be determined by the dideoxy sequencing method, dideoxy chain termination method, or the like. For example, this can be carried out using ABI PRISM Dye Terminator Cycle Sequencing Ready Reaction Kit (product of PerkinElmer) and ABI 373A DNA Sequencer (product of PerkinElmer).

Once part of the base sequence of the polynucleotide coding for said polypeptide has become clear, the base sequence of the whole can be determined, for example, by the i-PCR method (Nucl. Acids Res., 16, 8186 (1988)). When the polynucleotide on the chromosomal DNA contains an intron or introns, the base sequence of the intron-free mature polynucleotide can be determined, for example, by the following method. Thus, first, from a microorganism to serve as the origin of the polynucleotide, mRNA of the microorganism is prepared by the conventional method of nucleotide isolation such as the method described in Current Protocols in Molecular Biology (John Wiley and Sons, Inc., 1989). Then, using this mRNA as a template, a mature polynucleotide is amplified by the RT-PCR method (Proc. Natl. Acad. Sci. USA, 85, 8998 (1988)) using nucleotide primers respectively having the sequences around the 5' and 3' ends of said polynucleotide that have been made clear in advance, and the base sequence of the mature polypeptide is determined in the same manner as described above.

As the vector used for introducing the nucleotide of the invention into a host microorganism and expressing the same in the host microorganism, any of vectors capable of expressing the gene in said nucleotide in an appropriate host microorganism may be used. As such vectors, there may be mentioned, for example, ones selected from among plasmid vectors, phage vectors and cosmid vectors. Further, shuttle vectors capable of gene exchange with another host strain may also be used.

Such vectors generally contain such regulatory factors as the lacUV5 promoter, trp promoter, trc promoter, tac promoter, lpp promoter, tufB promoter, recA promoter and pL promoter and can be suitably used as expression vectors containing an expression unit operatively connected with the polynucleotide of the invention.

The term "regulatory factors" as used herein means a base sequence comprising a functional promoter and arbitrary related transcription elements (e.g. enhancer, CCAAT box, TATA box, SPI locus).

The phrase "operatively connected" as used herein means that the polynucleotide is connected with various regulatory elements controlling the expression thereof, inclusive of a promoter, an enhancer and so forth, so that the whole can operate in host cells and the gene in said polynucleotide can be expressed. It is well known to those skilled in the art that the types and species of the regulatory factors may vary according to the host cells.

As the host cells into which the expression vector containing the polynucleotide of the invention is to be introduced, there may be mentioned bacteria, yeasts, fungi, plant cells and animal cells, and the like. *Escherichia coli* cells are particularly preferred, however. The expression vector containing the polynucleotide of the invention can be introduced into host cells in the conventional manner. When *Escherichia coli* cells are used as the host cells, the expression vector containing the polynucleotide of the invention can be introduced thereinto by the calcium chloride method, for instance.

When (R)-2-chloro-1-(3'-chlorophenyl)ethanol is to be produced by asymmetrically reducing 2-chloro-1-(3'-chlorophenyl)ethanone using the polypeptide of the invention, a coenzyme such as NADPH or NADH is required. However, when an enzyme capable of converting the oxidized coenzyme to the reduced form (such ability hereinafter referred to as "coenzyme regenerating ability") is added to the reaction system together with the substrate thereof, namely when the reaction is carried out using the coenzyme regenerating system in combination with the polypeptide of the invention, the usage of the expensive coenzyme can be markedly reduced.

Usable as the enzyme having coenzyme regenerating ability are, for example, hydrogenase, formate dehydrogenase, alcohol dehydrogenase, aldehyde dehydrogenase, glucose-6-phosphate dehydrogenase and glucose dehydrogenase. Glucose dehydrogenase is preferably used.

The asymmetric reduction reaction can be carried out by separately adding the above-mentioned enzyme having coenzyme regenerating ability to the reaction system. It is possible to carry out the reaction efficiently by using, as a catalyst, a transformant as transformed with both the polynucleotide of the invention and a polynucleotide coding for a polypeptide having coenzyme regenerating ability, without separately preparing an enzyme having coenzyme regenerating ability and adding the same to the reaction system.

Such a transformant can be obtained by inserting the polynucleotide of the invention and a polynucleotide coding for a polypeptide having coenzyme regenerating ability (e.g. glucose dehydrogenase) into one and the same vector and introducing the resulting recombinant vector into host cells or, further, by inserting these two polynucleotides respectively into two vectors belonging to different incompatible groups and introducing the resulting two vectors into the same host cells.

The expression vector of the invention contains the above-mentioned polynucleotide, as described above. As a preferred example of the expression vector, there may be mentioned a plasmid pNTRG.

As the expression vector, there may also be mentioned one further containing a polynucleotide coding for the above-mentioned polypeptide having glucose dehydrogenase activity. The *Bacillus megaterium*-derived glucose dehydrogenase is preferred as the polypeptide having glucose dehydrogenase activity. More preferred is an expression vector which is a plasmid pNTRGG1.

The transformant of the invention is obtained by transforming host cells using the above expression vector. *Escherichia coli* cells are preferred as the host cells.

*E. coli* HB101(pNTRG) and *E. coli* HB101(pNTRGG1), which are typical transformants of the invention, have been internationally deposited, as of Jan. 22, 2002, with the National Institute of Advanced Industrial Science and Technology International Patent Organism Depositary, Central 6, 1-1-1 Higashi, Tsukuba, Ibaraki, Japan, under the accession numbers FERM BP-7857 and FERM BP-7858, respectively, under the Budapest Treaty.

The activity of the enzyme having coenzyme regenerating ability in the transformant can be measured in the conventional manner. For example, the glucose dehydrogenase activity can be determined by adding 0.1 M of the substrate glucose, 2 mM of the coenzyme NADP and the enzyme to 1 M Tris hydrochloride buffer (pH 8.0) and measuring the increment in absorbance at a wavelength 340 nm at 25° C.

The production of an optically active alcohol, such as an optically active 1-phenylethanol derivative or a 3-hydroxy ester derivative, using the transformant of the invention can be carried out as follows. That is, the culture of the above transformant or a processed product thereof is reacted with a carbonyl group-containing compound to obtain an optically active alcohol.

More specifically, the carbonyl group-containing compound to serve as the substrate, such a coenzyme as NADP and the culture of the transformant or a processed product thereof, and the like are first added to an appropriate solvent, and the reaction is allowed to proceed with stirring under pH adjustment.

The transformant can be cultivated using liquid nutrient media containing ordinary carbon sources, nitrogen sources, inorganic salts, organic nutrients and so forth so long as the microorganism can grow thereon. The cultivation temperature is preferably 4 to 50° C.

As the processed product of the transformant there may be mentioned, for example, crude extracts, cultured cells, lyophilized cells, acetone-dried cells, and products derived therefrom by grinding. It is also possible to use the polypeptide itself or cells as such in a form immobilized by a method known in the art.

When a transformant producing both the polypeptide of the invention and an enzyme having coenzyme regenerating ability (e.g. glucose dehydrogenase) is used in carrying out the reaction, it is possible to markedly reduce the amount of use of the coenzyme by adding, to the reaction system, a substrate (e.g. glucose) for coenzyme regeneration.

As the carbonyl group-containing compound, which is the substrate, there may be mentioned, for example, 1-phenylethanone derivatives represented by the formula (3):

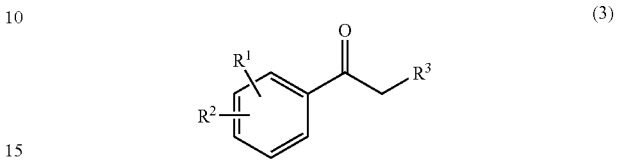

in the formula, $R^1$ and $R^2$ may be the same or different and each represents a hydrogen or halogen atom or an alkoxy or nitro group, $R^3$ represents a hydrogen or halogen atom, a hydroxyl group or an alkyl group, which may optionally be substituted, or 3-oxo ester derivatives represented by the formula (7):

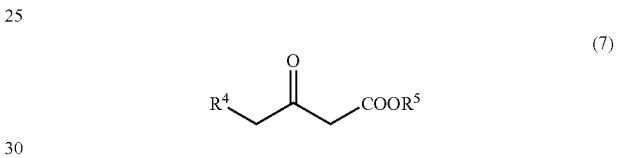

in the formula, $R^4$ represents a hydrogen or halogen atom, an azido or benzyloxy group or an alkyl group, which may optionally be substituted, and $R^5$ represents an alkyl or phenyl group. More specifically, there may be mentioned, for example, 2-chloro-1-(3'-chlorophenyl)ethanone, 1-(2'-fluorophenyl)ethanone, ethyl 4-chloroacetoacetate, and the like.

As the optically active alcohol obtainable by the method mentioned above there may be mentioned, for example, optically active 1-phenylethanol derivatives represented by the formula (4):

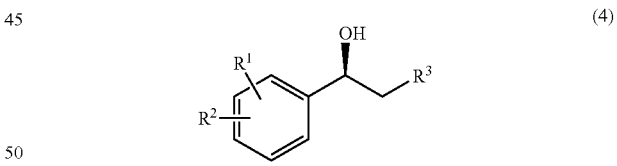

in the formula, $R^1$, $R^2$ and $R^3$ are as defined above, or optically active 3-hydroxy ester derivatives represented by the formula (8):

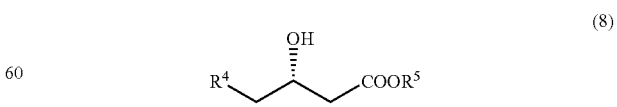

in the formula, $R^4$ and $R^5$ are as defined above. More specifically, there may be mentioned, for example, (R)-2-chloro-1-(3'-chlorophenyl)ethanol, (S)-1-(2'-fluorophenyl) ethanol, ethyl (R)-4-chloro-3-hydroxybutyrate, and the like.

As the halogen atom represented by $R^1$, $R^2$, $R^3$ and/or $R^4$, there may be mentioned, for example, a fluorine, chlorine, bromine or iodine atom.

As the alkoxy group represented by $R^1$ and/or $R^2$, there may be mentioned alkoxy groups containing 1 to 3 carbon atoms, for example, methoxy, ethoxy, propoxy group, etc., with methoxy group being preferred.

As the alkyl group represented by $R^3$, $R^4$ and/or $R^5$, there may be mentioned alkyl groups containing 1 to 8 carbon atoms, for example methyl, ethyl, propyl, hexyl, octyl group, etc. Preferred is an alkyl group containing 1 or 2 carbon atoms.

The alkyl group represented by $R^3$ and/or $R^4$ may optionally be substituted. As the substituent(s), there may be mentioned fluorine, chlorine and bromine atoms, hydroxyl and amino groups, and the like.

The solvent to be used in carrying out the reaction may be an aqueous solvent or a mixture of an aqueous solvent and an organic solvent. As the organic solvent, there may be mentioned, for example, toluene, hexane, diisopropyl ether, n-butyl acetate, ethyl acetate, and the like.

The reaction temperature is 10° C. to 70° C., preferably 20 to 40° C., and the reaction time is 1 to 100 hours, preferably 10 to 50 hours. During the reaction, the pH of the reaction mixture is maintained at 4 to 10, preferably 5 to 8, using an aqueous solution of sodium hydroxide, an aqueous solution of sodium carbonate, for instance.

Furthermore, the reaction can be carried out either batchwise or continuously. In the batchwise case, the reaction substrate is added to a charge concentration of 0.1% to 70% (w/v)

The optically active alcohol formed by the reaction can be purified in the conventional manner. When the optically active alcohol formed by the reaction is (R)-2-chloro-1-(3'-chlorophenyl)ethanol, (S)-1-(2'-fluorophenyl)ethanol or ethyl (R)-4-chloro-3-hydroxybutyrate, for instance, the suspended matter including microbial cells is removed from the reaction mixture by centrifugation, filtration or like treatment according to need, the product is then extracted with such an organic solvent as ethyl acetate or toluene, and the organic solvent is then removed under reduced pressure. The product can be further purified by subjecting to such a treatment as distillation and/or chromatography.

The quantitation of 2-chloro-1-(3'-chlorophenyl)ethanone and 2-chloro-1-(3'-chlorophenyl)ethanol and the determination of the optical purity of 2-chloro-1-(3'-chlorophenyl)ethanol can be carried out by high-performance liquid column chromatography (column: Daicel Chemical Industries' Chiralcel OJ (ID 4.6 mm×250 mm), eluent: n-hexane/isopropanol=39/1, flow rate: 1 ml/min, detection: 210 nm, column temperature: room temperature).

1-(2'-Fluorophenyl)ethanone and 1-(2'-fluorophenyl)ethanol can be quatitated by high-performance liquid column chromatography (column: Nacalai Tesque's COSMOSIL 5C8-MS (ID 4.6 mm×250 mm), eluent: water/acetonitrile=1/1, flow rate: 1 ml/min, detection: 210 nm, column temperature: room temperature).

The optical purity of 1-(2'-fluorophenyl)ethanol can be measured by high-performance liquid column chromatography (column: Daicel Chemical Industries' Chiralcel OB (ID 4.6 mm×250 mm), eluent: n-hexane/isopropanol=9/1, flow rate: 0.5 ml/min, detection: 254 nm, column temperature: room temperature).

Ethyl 4-chloroacetoacetate and ethyl 4-chloro-3-hydroxybutyrate can be quantitated by gas chromatography (column: GL Sciences Inc.'s PEG-20M Chromosorb WAW DMCS 10% 80/100 mesh (ID 3 mm×1 m), column temperature: 150° C., detection: FID).

The optical purity of ethyl 4-chloro-3-hydroxybutyrate can be determined by high-performance liquid column chromatography (column: Daicel Chemical Industries' Chiralcel OB (ID 4.6 mm×250 mm), eluent: n-hexane/isopropanol=9/1, flow rate: 0.8 ml/min, detection: 215 nm, column temperature: room temperature).

In accordance with the present invention, the polypeptide of the invention can be produced in an efficient manner and a method for producing various useful optically active alcohols is provided, as described above.

BRIEF DESCRITPION OF THE DRAWINGS

FIG. 1 shows the polynucleotide sequence of the invention and the amino acid sequence deduced therefrom.

BEST MODE FOR CARRYING OUT THE INVENTION

Figure 2:
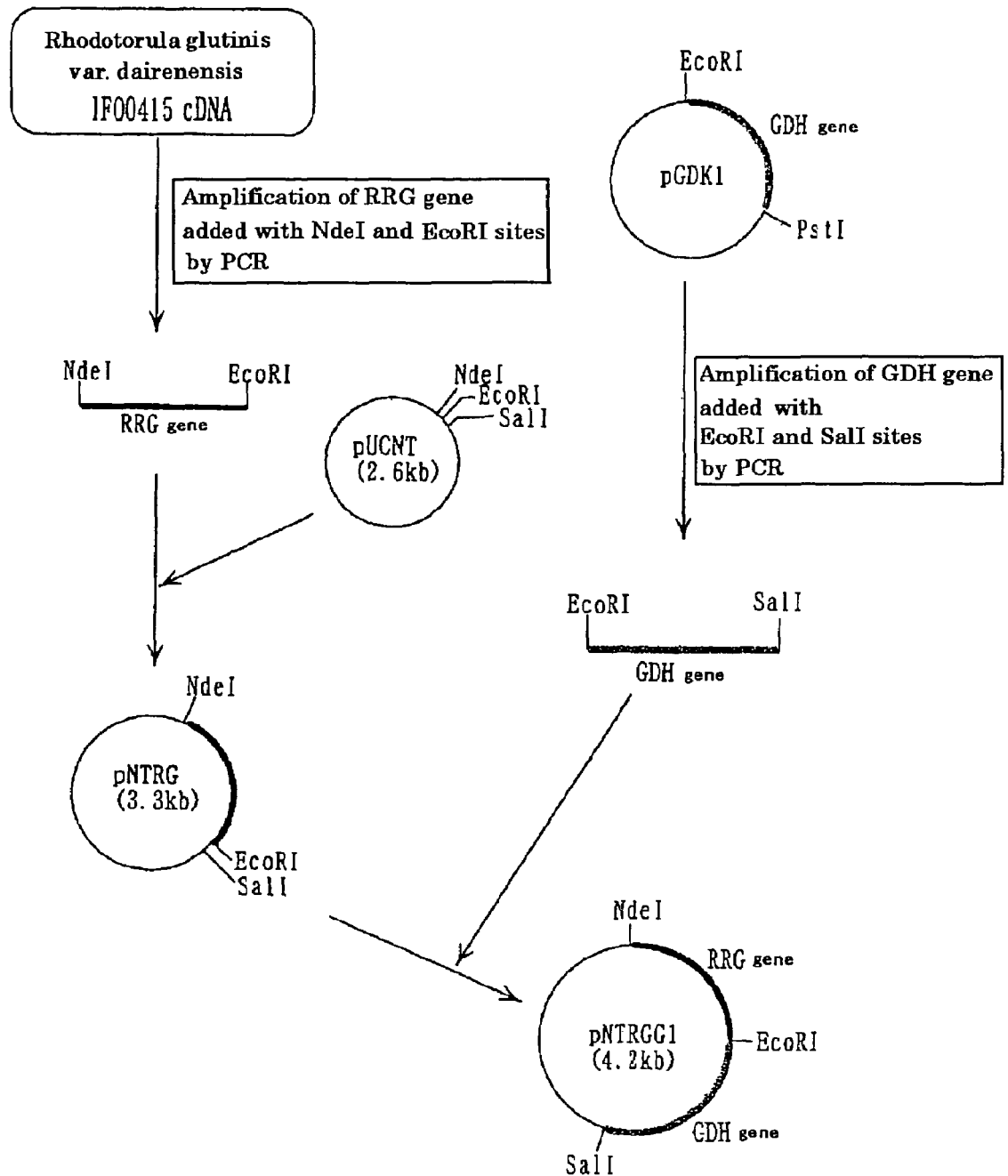
FIG. 2 shows a method for constructing a recombinant plasmid pNTRGG1 and the structure thereof.

The following examples illustrate the present invention in detail. They are, however, by no means limitative of the scope of the invention.

The details of the procedures in the recombinant DNA technology as used in the following examples are described in the following monographs: Molecular Cloning, 2nd Edition (Cold Spring Harbor Laboratory Press, 1989); Current Protocols in Molecular Biology (Greene Publishing Associates and Wiley-Interscience).

EXAMPLE 1

Enzyme Purification

An enzyme having activity in asymmetrically reducing 2-chloro-1-(3'-chlorophenyl)ethanone to form (R)-2-chloro-1-(3'-chlorophenyl)ethanol was singly purified from *Rhodotorula glutinis* var. *dairenensis* IFO 0415. Unless otherwise specified, the purification procedure was carried out at 4° C.

(Cultivation of *Rhodotorula glutinis* var. *dairenensis* IFO 0415)

18 L of a liquid medium having the composition specified below was prepared in a 30 L jar fermenter (product of B.E. Marubishi Co., Ltd.) and subjected to steam sterilization at 120° C. for 20 minutes.

Medium Composition (% Being Indicated as (w/v)):

| | |
|---|---|
| Glucose | 4.0% |
| Yeast extract | 0.3% |
| $KH_2PO_4$ | 0.7% |
| $(NH_4)_2HPO_4$ | 1.3% |
| NaCl | 0.1% |
| $MgSO_4.7H_2O$ | 0.08% |
| $ZnSO_4.7H_2O$ | 0.006% |
| $FeSO_4.7H_2O$ | 0.009% |
| $CuSO_4.5H_2O$ | 0.0005% |
| $MnSO_4.4$ to $6H_2O$ | 0.001% |
| Adekanol LG-109 (product of NOF Corp.) | 0.01% |
| Tap water | pH 7.0 |

This medium was inoculated with a culture containing *Rhodotorula glutinis* var. *dairenensis* IFO 0415 by 180 ml which has been precultured in advance in the same medium, and cultivation was carried out at a rate of stirring of 250 rpm, a rate of aeration of 5.0 NL/min. and a temperature of 30° C., while the pH was adjusted to a level not lower than 5.5 (lower limit) by dropwise addition of a 30% (w/w) aqueous solution of sodium hydroxide. After the lapse of 18 hours, 22 hours and 26 hours from the start of cultivation, 655 g of a 55% (w/w) aqueous solution of glucose was added on each occasion, and cultivation was carried out for 30 hours.

(Preparation of a Cell-free Extract)

Cells were collected from a 5,600 ml portion of the above culture by centrifugation and washed with 1,000 ml of 100 mM phosphate buffer (pH 8.2). Thus were obtained 1,599 g of wet cells of the strain mentioned above. The wet cells were suspended in 100 mM phosphate buffer (pH 8.2) to obtain 2,000 ml of a cell suspension. The cells in this suspension were disrupted in DYNO-Mill (product of Willy A. Bachofen Company), and the disruption product was deprived of cell residue by centrifugation to obtain 1,470 ml of cell-free extract.

(Ammonium Sulfate Fractionation)

Ammonium sulfate was added to and dissolved in the cell-free extract obtained in the above manner to attain 45% saturation, and the resulting precipitate was removed by centrifugation (on that occasion, the pH of the cell-free extract was maintained at 7.5 with aqueous ammonia). While maintaining the pH at 7.5 in the same manner as in the above step, ammonium sulfate was further added to and dissolved in the supernatant resulting from centrifugation to attain 60% saturation, and the resulting precipitate was collected by centrifugation. This precipitate was dissolved in 10 mM phosphate buffer (pH 7.5), and the solution was dialyzed overnight with the same buffer.

(DEAE-TOYOPEARL Column Chromatography)

The crude enzyme solution obtained in the above manner was applied, for enzyme adsorption, to a DEAE-TOYOPEARL 650 M (product of Tosoh Corporation) column (250 ml) equilibrated in advance with 10 mM phosphate buffer (pH 7.5). The column was washed with the same buffer, and an active fraction was then eluted at a linear gradient of NaCl (from 0 M to 0.3 M). The active fraction was collected and dialyzed overnight with 10 mM phosphate buffer (pH 7.5).

(Phenyl-TOYOPEARL Column Chromatography)

Ammonium sulfate was dissolved in the crude enzyme solution obtained in the above manner to a final concentration of 1 M (while maintaining the pH of the crude enzyme solution at 7.5 with aqueous ammonia), and the solution was applied, for enzyme adsorption, to a Phenyl-TOYOPEARL 650 M (product of Tosoh Corporation) column (100 ml) equilibrated in advance with 10 mM phosphate buffer (pH 7.5) containing 1 M ammonium sulfate. After washing the column with the same buffer, the active fraction was eluted at a linear gradient of ammonium sulfate (from 1 M to 0 M). The active fraction was collected and dialyzed overnight with 10 mM phosphate buffer (pH 7.5).

(Blue Sepharose Column Chromatography)

The crude enzyme solution obtained as described above was applied, for enzyme adsorption, to a Blue Sepharose CL-6B (product of Pharmacia Biotech) column (20 ml) equilibrated in advance with 10 mM phosphate buffer (pH 7.5). After washing the column with the same buffer, the active fraction was eluted at a linear gradient of NaCl (from 0 M to 1 M). The active fraction was collected and dialyzed overnight with 10 mM phosphate buffer (pH 7.5) to obtain a purified enzyme preparation showing a single spot in electrophoresis. Hereinafter, this enzyme is referred to as RRG.

EXAMPLE 2

Determination of Enzyme Properties

The enzyme obtained was investigated as to its enzymatic properties.

Fundamentally, the enzyme activity was measured by adding the substrate 2-chloro-1-(3'-chlorophenyl)ethanone (1 mM), the coenzyme NADPH (0.25 mM) and the enzyme to 100 mM phosphate buffer (pH 6.5) containing 0.3% (v/v) dimethyl sulfoxide, allowing the reaction to proceed at 30° C. for 1 minute, and then measuring the decrease in absorbance at a wavelength of 340 nm.

(1) Activity:

In the presence of NADPH as a coenzyme, the enzyme acted on 2-chloro-1-(3'-chlorophenyl)ethanone to form (R)-2-chloro-1-(3'-chlorophenyl)ethanol with an optical purity of 99.9% ee or more. The enzyme activity measured with NADH as a coenzyme by the above method was about 7% of the activity obtained by using NADPH as a coenzyme.

(2) Optimum pH for Activity:

Enzyme activity measurements were carried out by the same enzyme activity measurement method as mentioned above except that the pH was varied in the range of 4.0 to 8.0 using, as the buffer, 100 mM phosphate buffer containing dimethyl sulfoxide and 100 mM acetate buffer. As a result, the optimum pH for the action on 2-chloro-1-(3'-chlorophenyl)ethanone was found to be 5.0 to 6.0.

(3) Optimum Temperature for Activity:

Enzyme activity measurements were carried out by the same enzyme activity measurement method as mentioned above except that the temperature was varied from 20° C. to 60° C. As a result, the optimum temperature for the action on 2-chloro-1-(3'-chlorophenyl)ethanone was found to be 40° C. to 50° C.

(4) Molecular Weight:

The purified enzyme was subjected to gel filtration chromatography analysis on Superdex 200 HR 10/30 (product of Amersham Pharmacia Biotech) using 50 mM phosphate buffer (pH 7.0) containing 150 mM sodium chloride at an eluent. As a result, this enzyme was found to have a molecular weight of about 40,000 as calculated from its relative retention time as compared with standard proteins. The subunit molecular weight of the enzyme was calculated from the mobility values relative to standard proteins as obtained by SDS-polyacrylamide gel electrophoresis. The subunit molecular weight of the enzyme was about 30,000.

EXAMPLE 3

RRG Gene Cloning (PCR Primer Preparation)

The purified enzyme RRG obtained in Example 1 was denatured in the presence of 8 M urea and then digested with *Achromobacter*-derived lysyl endopeptidase (product of Wako Pure Chemical Industries, Ltd.). The amino acid sequences of the resulting peptide fragments were determined using a model ABI 492 protein sequencer (product of PerkinElmer). Based on these amino acid sequences, two DNA primers (primer 1, SEQ ID NO:3; primer 2, SEQ ID NO:4) were synthesized in the conventional manner.

(RRG Gene Amplification by PCR)

Chromosomal DNA was extracted from cultured cells of *Rhodotorula glutinis* var. *dairenensis* IFO 0415 by the method of Visser et al. (Appl. Microbiol. Biotechnol., 53, 415 (2000)). Then, using the DNA primers prepared as described above, PCR was carried out with the chromosomal DNA obtained as a template. A DNA fragment, about 600 bp in size and supposed to be part of the RRG gene, was amplified (PCR was carried out using TaKaRa Ex Taq (product of Takara Shuzo Co., Ltd.) as DNA polymerase under the reaction conditions described in the manual attached thereto). This DNA fragment was cloned in the plasmid pT7Blue T-Vector (product of Novagen), and the base sequence thereof was confirmed using the ABI PRISM Dye Terminator Cycle Sequencing Ready Reaction Kit (product of PerkinElmer) and the ABI 373A DNA Sequencer (product of PerkinElmer).

(Full-length Sequence Determination of the RRG Gene by i-PCR)

The chromosomal DNA of *Rhodotorula glutinis* var. *dairenensis* IFO 0415 was completely digested with the restriction enzyme SphI, and the DNA fragment mixture obtained was subjected to intramolecular cyclization using T4 ligase. Using the cyclization product as a template, the full-length base sequence of the RRG gene on the chromosomal DNA was determined by the i-PCR technique (Nucl. Acids Res., 16, 8186 (1988)) based on the partial base sequence information about the RRG gene as revealed in the above paragraph (PCR was carried out using TaKaRa LA PCR Kit Ver. 2 (product of Takara Shuzo Co., Ltd.)) under the conditions described in the manual attached thereto. The base sequence determination was made as described hereinabove.). The base sequence determined is shown under SEQ ID NO:9 in the sequence listing and in FIG. 1. In FIG. 1, the underlined portion is thought to be the section encoding the RRG gene in the base sequence, and the other portions to be introns. The amino acid sequence encoded by the underlined base sequence portion is shown below the base sequence. Comparison of this amino acid sequence with the partial amino acid sequences of the lysyl endopeptidase-digested fragments revealed that the partial amino acid sequences of the purified RRG were all found in this amino acid sequence. The underlined portions in the amino acid sequence shown in FIG. 1 are the portions showing coincidence with the partial amino acid sequences of the purified RRG.

EXAMPLE 4

Intron-free RRG Gene Acquisition

Based on the base sequence determined in Example 3, an N-terminal DNA primer (primer 3, SEQ ID NO:5) resulting from addition of an NdeI site to the initiation codon moiety of the RRG gene and a C-terminal DNA primer (primer 4, SEQ ID NO:6) resulting from addition of a termination codon (TAA) and an EcoRI site to just behind the 3' terminus of the same gene were synthesized. Then, the total RNA of *Rhodotorula glutinis* var. *dairenensis* IFO 0415 was extracted and purified from cultured cells of that strain using RNeasy Maxi Kit (product of QIAGEN). Using this RNA as a template and using the two DNAs prepared previously as primers, the intron-free mature type RRG gene with an NdeI site added to the initiation codon moiety and a termination codon (TAA) and an EcoRI cleavage site added just behind the 3' terminus was amplified by the RT-PCR method (Proc. Natl. Acad. Sci. USA, 85, 8998 (1988)) (RT-PCR was carried out using High Fidelity RNA PCR Kit (product of Takara Shuzo Co., Ltd.) under the reaction conditions described in the manual attached thereto.).

EXAMPLE 5

Construction of an RRG Gene-containing Recombinant Plasmid

The DNA fragment obtained in Example 4 was digested with NdeI and EcoRI, and the resulting fragment was inserted into the plasmid pUCNT (WO 94/03613, U.S. Pat. No. 6,083,752) at the NdeI, EcoRI site downstream from the lac promoter to obtain a recombinant plasmid pNTRG.

EXAMPLE 6

Construction of a Recombinant Plasmid Containing Both the RRG Gene and the Glucose Dehydrogenase Gene A double-stranded DNA derived from the *Bacillus megaterium* IAM 1030-derived glucose dehydrogenase (hereinafter referred to as "GDH") gene by addition of the *Escherichia coli*-derived Shine-Dalgarno sequence (9 bases) at a site 5 bases upstream of the initiation codon of that gene and a SacI cleavage site just before that sequence and, further, a BamHI cleavage site just behind the termination codon was obtained in the following manner. Based on the base sequence information about the GDH gene, an N-terminal DNA primer (primer 5, SEQ ID NO:7) resulting from addition of the *Escherichia coli*-derived Shaine-Dalgarno sequence (9 bases) at 5 bases upstream of the initiation codon of the structural gene for GDH and further addition of an EcoRI cleavage site just before that sequence and a C-terminal DNA primer (primer 6, SEQ ID NO:8) resulting from addition of a SalI site just behind the termination codon of the structural gene for GDH were synthesized in the conventional manner. Using these two DNA primers and using the plasmid pGDK1 (Eur. J. Biochem., 186, 389 (1989)) as a template, a double-stranded DNA was synthesized by PCR. The DNA fragment obtained was digested with EcoRI and SalI, and the digest was inserted into the pNTRG constructed in Example 5 at the EcoRI, SalI site (occurring downstream from the RRG gene) to obtain a recombinant plasmid pNTRGG1. The construction scheme for and the structure of pNTRGG1 are shown in FIG. 2.

EXAMPLE 7

Recombinant *Escherichia coli* Production

The recombinant plasmids pNTRG and pNTRGG1 obtained in Examples 5 and 6 were used to transform *Escherichia coli* HB101 (product of Takara Shuzo Co., Ltd.) to obtain transformant *Escherichia coli* strains HB101 (pNTRG) and HB101 (pNTRGG1), respectively. The thus-obtained transformants *Escherichia coli* HB101 (pNTRG) and HB101 (pNTRGG1) have been deposited, as of Jan. 22, 2002, with the National Institute of Advanced Industrial Science and Technology International Patent Organism Depositary, Central 6, 1-1-1 Higashi, Tsukuba, Ibaraki, Japan, under the accession numbers FERM BP-7857 and FERM BP-7858, respectively.

EXAMPLE 8

RRG Expression in Recombinant *Escherichia coli* Species

The recombinant *Escherichia coli* strain HB101 (pNTRG) obtained in Example 7 was cultivated in 2×YT medium containing 120 µg/ml of ampicillin. Cells were collected and then suspended in 100 mM phosphate buffer (pH 6.5) and disrupted using a model UH-50 ultrasonic homogenizer (product of SMT Co., Ltd.) to obtain a cell-free extract. The RRG activity of this cell-free extract was determined in the following manner. The RRG activity was determined by adding the substrate 2-chloro-1-(3'-chlorophenyl)ethanone (1 mM), the coenzyme NADPH (0.25 mM) and the enzyme to 100 mM phosphate buffer (pH 6.5) containing 0.3% (v/v) of dimethyl sulfoxide, and measuring the decrease in absorbance at a wavelength of 340 nm at 30° C. The enzyme activity oxidizing 1 µmol of NADPH to NADP per minute under these reaction conditions was defined as 1 unit. The thus-measured RRG activity in the cell-free extract was expressed in terms of specific activity and compared with that of the vector plasmid-harboring transformant. Similarly, the RRG activity in the cell-free extract from *Rhodotorula glutinis* var. *dairenensis* IFO 0415 as prepared in the same manner as in Example 1 was determined for comparison. The results of those determinations are shown in Table 1. A distinct increase in RRG activity was observed in *Escherichia coli* HB101 (pNTRG) as compared with *Escherichia coli* HB101 (pUCNT) harboring the vector plasmid alone, and the specific activity was about 150 times higher as compared with *Rhodotorula glutinis* var. *dairenensis* IFO 0415.

TABLE 1

| Microbial strain | RRG specific activity (U/mg) |
|---|---|
| *E. coli* HB101 (pUCNT) | <0.01 |
| *E. coli* HB101 (pNTRG) | 12.4 |
| *Rhodotorula glutinis* var. *dairenensis* IF00415 | 0.08 |

EXAMPLE 9

Simultaneous Expression of RRG and GDH in Recombinant *Escherichia coli* Strains The recombinant *Escherichia coli* strain HB101 (pNTRGG1) obtained in Example 7 was treated in the same manner as in Example 8, and the cell-free extract obtained was assayed for GDH activity in the following manner. The GDH activity was measured by adding the substrate glucose (0.1 M), the coenzyme NADP (2 mM) and the enzyme to 1 M Tris-hydrochloride buffer (pH 8.0) and measuring the increase in absorbance at a wavelength of 340 nm at 25° C. The enzyme activity reducing 1 µmol of NADP to NADPH per minute under these reaction conditions was defined as 1 unit. The RRG activity was also measured in the same manner as in Example 8. The thus-measured RRG and GDH activities of the cell-free extract were each expressed in terms of specific activity and compared with the results with *Escherichia coli* HB101 (pNTRG) and the transformant HB101 (pUCNT) harboring the vector plasmid alone. The comparative results are shown in Table 2. With *Escherichia coli* HB101 (pNTRGG1), distinct increases in RRG activity and GDH activity were found as compared with the transformant *Escherichia coli* HB101 (pUCNT) harboring the vector plasmid alone.

TABLE 2

| Microbial strain | RRG specific activity (U/mg) | GDH specific activity (U/mg) |
|---|---|---|
| *E. coli* HB101 (pUCNT) | <0.01 | <0.01 |
| *E. coli* HB101 (pNTRG) | 12.4 | <0.01 |
| *E. coli* HB101 (pNTRGG1) | 7.56 | 128 |

EXAMPLE 10

Synthesis of (R)-2-chloro-1-(3'-chlorophenyl)ethanol from 2-chloro-1-(3'-chlorophenyl)ethanone using the Recombinant *Escherichia coli* Strain Introduced with the RRG Gene The culture of the recombinant *Escherichia coli* HB101 (pNTRG) as obtained in Example 8 was subjected to ultrasonic cell disruption using SONIFIRE 250 (product of BRANSON). To 20 ml of this cell disruption fluid, there were added 2,000 U of glucose dehydrogenase (product of Amano Pharmaceutical Co., Ltd.), 3 g of glucose, 2 mg of NADP and 2 g of 2-chloro-1-(3'-chlorophenyl)ethanone. This reaction mixture was stirred at 30° C. for 18 hours while adjusting the pH to 6.5 by addition of 5 M sodium hydroxide. After completion of the reaction, this reaction mixture was extracted with toluene, the solvent was then removed, and the extract was analyzed. 2-Chloro-1-(3'-chlorophenyl)ethanol was obtained in 96% yield. The 2-chloro-1-(3'-chlorophenyl)ethanol formed on that occasion was the R form with an optical purity of 99.9% ee.

The quantitation of 2-chloro-1-(3'-chlorophenyl)ethanone and of 2-chloro-1-(3'-chlorophenyl)ethanol and the optical purity measurement of 2-chloro-1-(3'-chlorophenyl)ethanol were carried out by high-performance liquid column chromatography (column: Daicel Chemical Industries' Chiralcel OJ (ID 4.6 mm×250 mm), eluent: n-hexane/isopropanol=39/1, flow rate: 1 ml/min, detection: 210 nm, column temperature: room temperature).

EXAMPLE 11

Synthesis of (R)-2-chloro-1-(3'-chlorophenyl)ethanol from 2-chloro-1-(3'-chlorophenyl)ethanone using the Recombinant *Escherichia coli* Strain for Simultaneous Expression of RRG and Glucose Dehydrogenase The culture of the recombinant *Escherichia coli* HB101 (pNTRGG1) as obtained in Example 9 was subjected to ultrasonic cell disruption using SONIFIRE 250 (product of BRANSON). To 20 ml of this cell disruption fluid, there were added 3 g of glucose, 2 mg of NADP and 2 g of 2-chloro-1-(3'-chlorophenyl)ethanone. This reaction mixture was stirred at 30° C. for 24 hours while adjusting the pH to 6.5 by dropwise addition of 5 M sodium hydroxide. After completion of the reaction, this reaction mixture was extracted with toluene, the solvent was then removed, and the extract was analyzed in the same manner as in Example 10. 2-Chloro-1-(3'-chlorophenyl)ethanol was obtained in 93% yield. The 2-chloro-1-(3'-chlorophenyl)ethanol formed on that occasion was the R form with an optical purity of 99.9% ee.

EXAMPLE 12

Synthesis of ethyl (R)-4-chloro-3-hydroxybutyrate from ethyl 4-chloroacetoacetate using the Recombinant *Escherichia coli* Strain for Simultaneous Expression of RRG and Glucose Dehydrogenase The culture of the recombinant *Escherichia coli* HB101 (pNTRGG1) as obtained in Example 9 was subjected to ultrasonic cell disruption using SONIFIRE 250 (product of BRANSON). To 20 ml of this cell disruption fluid, there were added 4 g of glucose and 3 mg of NADP. While stirring this reaction mixture at 30° C. and adjusting the pH to 6.5 by dropwise addition of 5 M sodium hydroxide, a total of 2 g of ethyl 4-chloroacetoacetate was added to the mixture continuously at a rate of 0.2 g per hour. After completion of the addition, the reaction was further allowed to proceed for 12 hours. After completion of the reaction, this reaction mixture was extracted with ethyl acetate, the solvent was then removed, and the extract was analyzed. Ethyl 4-chloro-3-hydroxybutyrate was obtained in 98% yield. The ethyl 4-chloro-3-hydroxybutyrate formed on that occasion was the R form with an optical purity of 99% ee or more.

The quantitation of ethyl 4-chloroacetoacetate and of ethyl 4-chloro-3-hydroxybutyrate was carried out by gas chromatography (column: GL Sciences Inc.'s PEG-20M Chromosorb WAW DMCS 10% 80/100 mesh (ID 3 mm×1 m), column temperature: 150° C., detection: FID). The optical purity of ethyl 4-chloro-3-hydroxybutyratre was determined by high-performance liquid column chromatography (column: Daicel Chemical Industries' Chiralcel OB (ID 4.6 mm×250 mm), eluent: n-hexane/isopropanol=9/1, flow rate: 0.8 ml/min, detection: 215 nm, column temperature: room temperature).

EXAMPLE 13

Synthesis of (S)-1-(2'-fluorophenyl)ethanol from 1-(2'-fluorophenyl)ethanone using the Recombinant *Escherichia coli* Strain for Simultaneous Expression of RRG and Glucose Dehydrogenase The culture of the recombinant *Escherichia coli* HB101 (pNTRGG1) as obtained in Example 9 was subjected to ultrasonic cell disruption using SONIFIRE 250 (product of BRANSON). To 100 ml of this cell disruption fluid, there were added 15 g of glucose, 5 g of 1-(2'-fluorophenyl)ethanone and 15 mg of NADP. This reaction mixture was stirred at 30° C. for 24 hours while adjusting the pH to 6.5 with 5 M sodium hydroxide. After completion of the reaction, this reaction mixture was extracted with ethyl acetate, the solvent was then removed, and the extract was distilled (54° C./1 mm Hg) to obtain 4.1 g of 1-(2'-fluorophenyl)ethanol as a colorless oil. Its specific rotation showed a value of [α] (25,D)=−45.3 (c=0.794, methanol) and it was the S form with an optical purity of 99.9% ee.

$^1$H-NMR (CDCl$_3$) δ ppm: 1.52 (d, 3H), 1.97 (br, 1H), 5.20 (q, 1H), 6.99 to 7.51 (m, 4H)

The quantitation of 1-(2'-fluorophenyl)ethanone and of 1-(2'-fluorophenyl)ethanol was carried out by high-performance liquid column chromatography (column: Nacalai Tesque's COSMOSIL 5C8-MS (ID 4.6 mm×250 mm), eluent: water/acetonitrile=1/1, flow rate: 1 ml/min, detection: 210 nm, column temperature: room temperature). The optical purity of 1-(2'-fluorophenyl)ethanol was determined by high-performance liquid column chromatography (column: Daicel Chemical Industries' Chiralcel OB (ID 4.6 mm×250 mm), eluent: n-hexane/isopropanol=9/1, flow rate: 0.5 ml/min, detection: 254 nm, column temperature: room temperature).

EXAMPLE 14

Substrate Specificity Features of RRG

RRG was examined for reducing activities against various carbonyl compounds. Thus, various carbonyl compounds specified in Table 3 were used as substrates in lieu of 2-chloro-1-(3'-chlorophenyl)ethanone and activity measurements were carried out under the basic reaction conditions for the RRG activity measurement in Example 2. The measurement results were expressed in terms of relative values with the reducing activity found with 2-chloro-1-(3'-chlorophenyl)ethanone as the substrate being taken as 100%. They are shown in Table 3.

TABLE 3

Substrate specificity features of the reductase RRG

| Reaction substrate | % Activity |
| --- | --- |
| 2-chloro-1-(3'-chlorophenyl)ethanone | 100 |
| 2-acetylpyridine | 60 |
| 3-acetylpyridine | 28 |
| 4-acetylpyridine | 44 |
| 1-benyl-3-pyrolidinone | 4 |
| m-hydroxyacetophenone | 16 |
| m-nitroacetophenone | 35 |
| p-chloroacetophenone | 5 |
| 4-fluoroacetophenone | 30 |
| 3,4-dimethoxyacetophenone | 46 |
| α,α,α-trifluoroacetophenon | 83 |
| 2-hydroxyacetophenone | 34 |
| propiophenone | 14 |
| n-butyrophenone | 8 |
| 1-phenyl-2-butanone | 20 |
| benzoin | 9 |
| trans-calcone | 22 |
| ethyl benzoylylacetate | 15 |
| acetone | 11 |
| 2-butanone | 10 |
| methyl n-propylketone | 12 |
| 2-hexanone | 13 |
| 2-heptanone | 11 |
| diethyl ketone | 17 |
| chloroacetone | 6 |
| hydroxyacetone | 16 |
| 4-hydroxy-2-butanone | 11 |
| diacetyl | 4 |
| acetylacetone | 23 |
| 4-methyl-2-pentanone | 10 |
| cyclopropyl methyl ketone | 3 |
| cyclopentanone | 9 |
| camphorquinone | 33 |
| tetrahydrofuran-2,4-dione | 14 |
| isophorone | 1 |
| dihydro-4,4-dimethyl-furandio | 238 |
| methyl 2-oxocyclopentane carboxylate | 11 |
| ethyl 3-oxocyclopentanecarboxylate | 32 |
| methyl pyrucvate | 208 |

TABLE 3-continued

Substrate specificity features of the reductase RRG

| Reaction substrate | % Activity |
| --- | --- |
| ethly pyruvate | 247 |
| methyl acetoacetate | 14 |
| ethyl acetoacetate | 35 |
| tert-butyl acetoacetate | 1 |
| ethyl 2-methylacetoacetate | 12 |
| ethyl 2-chloroacetoacetate | 111 |
| methyl 2-eteneacetoacetate | 5 |
| methyl 2-oxooctanoate | 3 |
| methyl 4-chloroacetoacetate | 81 |
| ethyl 4-chloroacetoacetate | 12 |
| n-octyl 4-chloroacetoacetate | 72 |
| ethyl 4-bromoacetoacetate | 33 |
| ethyl 4-azideacetoacetate | 11 |
| ethyl 4-hydroxyacetoacetate | 22 |
| ethyl 4-benzyloxyacetoacetate | 58 |
| ethyl 4-acetoxyacetoacetate | 46 |
| benzyl acetoacetate | 30 |
| ethyl 2-chloro-3-oxo-3-phen propionate | 34 |
| benzaldehyde | 25 |
| 2-pyridinecarbaldehyde | 45 |
| pyridine-4-aldehyde | 55 |
| o-chlorobenzaldehyde | 24 |
| m-chlorobenzaldehyde | 45 |
| p-chlorobenzaldehyde | 11 |
| o-nitrobenzaldehyde | 31 |
| m-nitrobenzaldehyde | 64 |
| p-nitrobenzaldhyde | 162 |
| propionaldehyde | 4 |
| n-butylaldhyde | 20 |
| n-hexylaldehyde | 10 |
| DL-glyceraldehyde | 1 |
| 3-phenylpropionaldehyde | 10 |
| methyl glyoxal | 13 |
| glutaraldehyde | 2 |
| 2-keto-n-butyric acid | 7 |
| oxalacetic acid | 24 |
| levulinic acid | 31 |

INDUSTRIAL APPLICABILITY

As a result of gene cloning of a polypeptide having activity in asymmetrically reducing 2-chloro-1-(3'-chlorophenyl)ethanone to form (R)-2-chloro-1-(3'-chlorophenyl)ethanol and analysis of the nucleotide sequence thereof, it has become possible to obtain a transformant highly capable of producing the polypeptide. It has also become possible to obtain a transformant capable of producing the polypeptide and glucose dehydrogenase simultaneously at high levels. Further, it has become possible to synthesize various optically active alcohols from the corresponding carbonyl compounds with good efficiency by using said transformant.

The invention claimed is:

1. An isolated polynucleotide encoding a polypeptide, wherein the polypeptide comprises the amino acid sequence of SEQ ID NO:1.

2. An isolated polynucleotide wherein:
   the polynucleotide comprises SEQ ID NO:2, or
   the polynucleotide is capable of hybridizing under stringent conditions with the nucleotide sequence complementary to the full length of SEQ ID NO:2 and encoding a polypeptide having activity in asymmetrically reducing 2-chloro-1-(3'-chlorophenyl)ethanone represented by the formula (1):

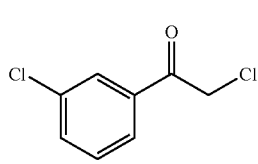
(1)

to form (R)-2-chloro-1-(3'-chlorophenyl)ethanol represented by the formula (2):

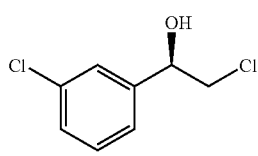
(2)

wherein said stringent conditions involve washing a filter with 0.1 to 2×SSC solution at a temperature of 65° C.

3. An expression vector comprising the polynucleotide according to claim 2.

4. The expression vector according to claim 3, wherein the expression vector is a plasmid pNTRG.

5. The expression vector according to claim 3, further comprising a polynucleotide encoding a polypeptide having glucose dehydrogenase activity.

6. The expression vector according to claim 5, wherein the polypeptide having glucose dehydrogenase activity is a *Bacillus megaterium*-derived glucose dehydrogenase.

7. The expression vector according to claim 6, wherein the expression vector is a plasmid pNTRGG1.

8. A transformant, resulting from transforming an isolated host cell with the expression vector according to claim 3.

9. The transformant according to claim 8, wherein the host cell is *Escherichia coli* (*E. coli*).

10. The transformant according to claim 9, wherein the transformant is *E. coli* HB101(pNTRG) (FERM BP-7857).

11. The transformant according to claim 9, wherein the transformant is *E. coli* HB101(pNTRGG1) (FERM BP-7858).

12. The isolated polynucleotide according to claim 2, wherein the polypeptide is derived from a microorganism belonging to the genus *Rhodotorula*.

13. The isolated polynucleotide according to claim 12, wherein the microorganism belonging to the genus *Rhodotorula* is *Rhodotorula glutinis* var. *dairenensis* IFO 0415.

14. A method of producing an optically active 1-phenylethanol derivative represented by the formula (4), comprising reacting the culture of the transformant according to claim 8, or a processed product thereof with a carbonyl group-containing compound represented by formula (3):

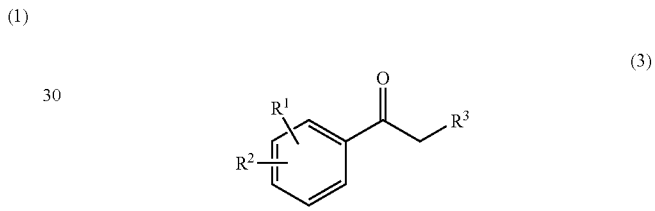
(3)

wherein,
R$^1$ and R$^2$ may be the same or different and each represents a hydrogen or halogen atom or an alkoxy or nitro group,
R$^3$ represents a hydrogen or halogen atom, a hydroxyl group or an alkyl group, which may optionally be substituted, the formula (4) being:

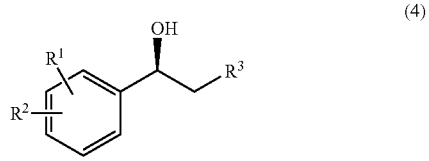
(4)

wherein, R$^1$, R$^2$ and R$^3$ are as defined above.

15. The method according to claim 14, wherein the carbonyl group-containing compound is 2-chloro-1-(3'-chlorophenyl)ethanone represented by the formula (1):

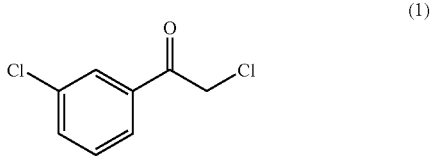
(1)

and the optically active alcohol is (R)-2-chloro-1-(3'-chlorophenyl)ethanol represented by the formula (2):

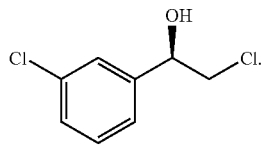

(2)

16. The method according to claim 14, wherein the carbonyl group-containing compound is 1-(2'-fluorophenyl)ethanone represented by the formula (5):

(5)

and the optically active alcohol is (S)-1-(2'-fluorophenyl)ethanol represented by the formula (6):

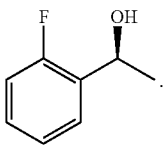

(6)

17. A method for producing optically active 3-hydroxyester derivative represented by formula (8), comprising reacting the culture of the transformant according to claim 8, or a processed product thereof with a carbonyl group-containing compound represented by formula (7):

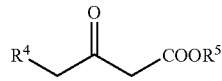

(7)

wherein,
R$^4$ represents a hydrogen or halogen atom, an azido or benzyloxy group or an alkyl group, which may optionally be substituted, and
R$^5$ represents an alkyl or phenyl group, the general formula (8) being:

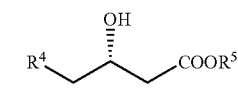

(8)

wherein, R$^4$ and R$^5$ are as defined above.

18. the method according to claim 17, wherein the carbonyl group-containing compound is ethyl 4-chloroacetoacetate represented by the formula (9):

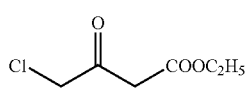

(9)

and the optically active alcohol is ethyl (R)-4-chloro-3-hydroxybutyrate represented by the formula (10):

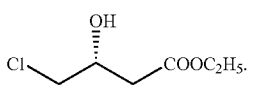

(10)

* * * * *

SEQUENCE LISTING

<160> NUMBER OF SEQ ID NOS: 9

<210> SEQ ID NO 1
<211> LENGTH: 249
<212> TYPE: PRT
<213> ORGANISM: Rhodotorula glutinis var.dairenensis

<400> SEQUENCE: 1

```
Met Pro Ala Ala Lys Thr Tyr Phe Ile Ser Gly Ala Ser Arg Gly Leu
  1               5                  10                  15

Gly Leu Gly Tyr Thr Arg Glu Leu Leu Ala Ser Asn Pro Asp Val Arg
             20                  25                  30

Val Val Ala Gly Val Arg Asn Pro Ser Asn Ala Gln Leu Leu Asp Ala
         35                  40                  45

Leu Ala Ala Glu Pro Ala Asn Lys Gly Arg Val His Val Ile Ala Trp
     50                  55                  60

Asp Val Asp His Glu Asp Lys Val Arg Glu Ser Ala Arg Glu Leu Glu
 65                  70                  75                  80

Thr Asn Pro Phe Val Lys Glu Ser Gly Ile Asp Thr Val Ile Val Asn
                 85                  90                  95

Ala Gly Val Phe Val Gly Gly His Lys Pro Pro Ala Glu Met Ser Met
            100                 105                 110

Asp Asp Leu Arg Ala Asn Phe Arg Thr Asn Val Glu Gly Ala Ile Phe
        115                 120                 125

Thr Val Gln Tyr Leu His Pro Leu Leu Glu Arg Gly Gln Ala Lys Gln
    130                 135                 140
```

```
Ile Phe Phe Ile Ser Ser Ile Val Gly Ser Met Gln Gly Phe Tyr Ser
145                 150                 155                 160

Gln Leu Ser Ala Gly Val Ser Tyr Ser Met Ser Lys Ala Ala Leu Asn
                165                 170                 175

Met Tyr Gly Val Lys Leu Ala Arg Glu Leu Gly Asp Lys Gly Tyr Thr
            180                 185                 190

Val Leu Leu Ile His Pro Gly Tyr Val Lys Thr Asp Met Asn Asn Phe
        195                 200                 205

Asp Gly Gly Asp Ile Thr Thr Glu Glu Ala Val Ser Leu Ala Thr
    210                 215                 220

Lys Asn Val Phe Leu Ala Ala Thr Pro Glu Trp Asn Gly Arg Tyr Ile
225                 230                 235                 240

Asp Tyr Glu Gly Lys Thr Val Pro Trp
                245
```

<210> SEQ ID NO 2
<211> LENGTH: 750
<212> TYPE: DNA
<213> ORGANISM: Rhodotorula glutinis var.dairenensis

<400> SEQUENCE: 2

```
atg ccc gca gca aag act tac ttc atc tcg ggc gcc tcg cgc ggc ctc        48
Met Pro Ala Ala Lys Thr Tyr Phe Ile Ser Gly Ala Ser Arg Gly Leu
1               5                   10                  15 gga ttg ggc tac acc cgt gaa ctg ctc gcc tcg aac cct gac gtc cga        96
Gly Leu Gly Tyr Thr Arg Glu Leu Leu Ala Ser Asn Pro Asp Val Arg
            20                  25                  30 gtc gtc gcc gga gtt cgc aac cct tct aac gcc cag ctc ttg gac gcc       144
Val Val Ala Gly Val Arg Asn Pro Ser Asn Ala Gln Leu Leu Asp Ala
        35                  40                  45 ctc gcc gcc gaa ccc gcc aac aaa ggc cga gtt cac gtc atc gcg tgg       192
Leu Ala Ala Glu Pro Ala Asn Lys Gly Arg Val His Val Ile Ala Trp
    50                  55                  60 gac gtc gac cac gag gac aag gtc cgc gag tcg gcg cgc gag ttg gaa       240
Asp Val Asp His Glu Asp Lys Val Arg Glu Ser Ala Arg Glu Leu Glu
65                  70                  75                  80 aca aac ccg ttc gtg aaa gag tct gga atc gac acc gtc atc gtc aac       288
Thr Asn Pro Phe Val Lys Glu Ser Gly Ile Asp Thr Val Ile Val Asn
                85                  90                  95 gca ggc gtc ttt gtc ggc gga cac aag ccg ccc gcc gag atg tcg atg       336
Ala Gly Val Phe Val Gly Gly His Lys Pro Pro Ala Glu Met Ser Met
            100                 105                 110 gac gac ctg cgc gcc aac ttc cgg acc aac gtc gag gga gcc atc ttt       384
Asp Asp Leu Arg Ala Asn Phe Arg Thr Asn Val Glu Gly Ala Ile Phe
        115                 120                 125 acc gtc cag tac ctc cac ccg ctg ctt gag cgt ggg cag gcg aag cag       432
Thr Val Gln Tyr Leu His Pro Leu Leu Glu Arg Gly Gln Ala Lys Gln
    130                 135                 140 atc ttc ttc atc agc tcg atc gtc ggg tcg atg cag ggc ttt tac tcg       480
Ile Phe Phe Ile Ser Ser Ile Val Gly Ser Met Gln Gly Phe Tyr Ser
145                 150                 155                 160 cag ctg tcg gcc ggc gtc tct tac tcc atg tcc aag gcc gcc ctg aac       528
Gln Leu Ser Ala Gly Val Ser Tyr Ser Met Ser Lys Ala Ala Leu Asn
                165                 170                 175 atg tac ggc gtc aag ctc gcg cgc gag ctc ggc gac aag ggc tac acg       576
Met Tyr Gly Val Lys Leu Ala Arg Glu Leu Gly Asp Lys Gly Tyr Thr
            180                 185                 190 gtc ctc ctg atc cac ccg ggc tac gtc aag acc gac atg aac aac ttt       624
Val Leu Leu Ile His Pro Gly Tyr Val Lys Thr Asp Met Asn Asn Phe
        195                 200                 205
```

-continued

```
              195                 200                 205
gac gga ggc gga gac atc acc acg gag gaa gcg gtt agc ctc gcg acg    672
Asp Gly Gly Gly Asp Ile Thr Thr Glu Glu Ala Val Ser Leu Ala Thr
        210                 215                 220 aaa aac gtc ttc ctc gcc gcc act ccc gag tgg aac ggc cgc tac atc    720
Lys Asn Val Phe Leu Ala Ala Thr Pro Glu Trp Asn Gly Arg Tyr Ile
225                 230                 235                 240 gac tac gag ggc aag acc gtg ccg tgg tag                            750
Asp Tyr Glu Gly Lys Thr Val Pro Trp
                245                 250

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer 1
<220> FEATURE:
<221> NAME/KEY: modified_base
<222> LOCATION: (6)
<223> OTHER INFORMATION: a, t, c, g, other or unknown

<400> SEQUENCE: 3
aaracntayt tyathtcrgg                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer 2
<220> FEATURE:
<221> NAME/KEY: modified_base
<222> LOCATION: (3)
<223> OTHER INFORMATION: a, t, c, g, other or unknown
<220> FEATURE:
<221> NAME/KEY: modified_base
<222> LOCATION: (12)
<223> OTHER INFORMATION: a, t, c, g, other or unknown

<400> SEQUENCE: 4
tgngartara anccytgcat                                              20

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Primer 3

<400> SEQUENCE: 5
gtgcatatgc ccgcagcaaa gacttac                                      27

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Primer 4

<400> SEQUENCE: 6
ggcgaattct tactaccacg gcacggtctt gc                                32

<210> SEQ ID NO 7
<211> LENGTH: 32
<212> TYPE: DNA
<213> ORGANISM: Artificial Sequence
```

```
<220> FEATURE:
<223> OTHER INFORMATION: Description of Artificial Sequence: Primer 5

<400> SEQUENCE: 7
gccgaattct aaggaggtta acaatgtata aa                                32

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence :Primer 6

<400> SEQUENCE: 8
gcggtcgact tatccgcgtc ctgcttgg                                     28

<210> SEQ ID NO 9
<211> LENGTH: 1195
<212> TYPE: DNA
<213> ORGANISM: Rhodotorula glutinis var. dairenensis
<220> FEATURE:
<221> NAME/KEY: intron
<222> LOCATION: (32)..(104)
<220> FEATURE:
<221> NAME/KEY: intron
<222> LOCATION: (403)..(493)
<220> FEATURE:
<221> NAME/KEY: intron
<222> LOCATION: (667)..(736)
<220> FEATURE:
<221> NAME/KEY: intron
<222> LOCATION: (751)..(818)
<220> FEATURE:
<221> NAME/KEY: intron
<222> LOCATION: (918)..(990)
<220> FEATURE:
<221> NAME/KEY: intron
<222> LOCATION: (1044)..(1113)

<400> SEQUENCE: 9
atgcccgcag caaagactta cttcatctcg ggtgcgtcca gcgaaaacca ggtctatccg    60
gtccaggtgc acacagaccc gctgacacag cttcactcgc gcaggcgcct cgcgcggcct   120
cggattgggc tacacccgtg aactgctcgc ctcgaaccct gacgtccgag tcgtggccgg   180
agttcgcaac ccttctaacg cccagctctt ggacgccctc gccgccgaac ccgccaacaa   240
aggccgagtt cacgtcatcg cgtgggacgt cgaccacgag gacaaggtcc gcgagtcggc   300
gcgcgagttg gaaacaaacc cgttcgtgaa agagtctgga atcgacaccg tcatcgtcaa   360
cgcaggcgtt tttgtcggcg gacacaagcc gcccgccgag atgtgagtcc gtagaacccg   420
cggccggtga cgaacgcccc gatcaataag tctcaacaga gccaccggag ctgagcgaga   480
aacgtaccca caggtcgatg gacgacctgc gcgccaactt ccggaccaac gtcgagggag   540
ccatctttac cgtccagtac ctccacccgc tgcttgagcg tgggcaggcg aagcagatct   600
tcttcatcag ctcgatcgtc gggtcgatgc agggcttttta ctcgcagctg tcggccggcg   660
tctcttgtga gcacgcttcc ccctgccgc ctttggtaca cgagctcgac tgacgcccac   720
attcccccac gaacagactc catgtccaag gttagtcccg ctcgagctct tgcgggccac   780
cgggaacctg accggctgcg ccgaaaactg cgtcacaggc cgccctgaac atgtacggcg   840
tcaagctcgc gcgcgagctc ggcgacaagg gctacacggt cctcctgatc cacccgggct   900
acgtcaagac cgacatggtg cgccttcgtt cgcttcaaag cgagtaatcg cgaatccttc   960
```

```
ccctcgctg  acatggtttc  cctccggcag  aacaactttg  acggaggcgg  agacatcacc    1020
acggaggaag  cggttagcct  cgcgtgcgtg  acaacgtatc  tccgtgatca  ggagcacggg    1080
acctcgcaag  ctgatcatcc  gcgctcgcga  caggacgaaa  aacgtcttcc  tcgccgccac    1140
tcccgagtgg  aacggccgct  acatcgacta  cgagggcaag  accgtgccgt  ggtag         1195
```